United States Patent
Haubrich

[19]

[11] Patent Number: 5,899,848
[45] Date of Patent: May 4, 1999

[54] DEVICE AND PROCESS FOR ARTIFICIAL INSEMINATION OF ANIMALS

[76] Inventor: Mark A. Haubrich, 35584 C-44, Le Mars, Iowa 51031

[21] Appl. No.: 08/891,923

[22] Filed: Jul. 14, 1997

[51] Int. Cl.$^6$ .................................................... A61B 17/43
[52] U.S. Cl. ................................................................ 600/35
[58] Field of Search ....................... 600/33–35; 119/174; 604/27, 30, 36, 37, 41–44, 48, 54, 55, 96–104

[56] References Cited

U.S. PATENT DOCUMENTS

| | | | |
|---|---|---|---|
| 4,403,603 | 9/1983 | Hutchins | 600/35 |
| 4,654,025 | 3/1987 | Cassou et al. | 604/55 X |
| 5,360,389 | 11/1994 | Chenette | 600/34 |
| 5,674,178 | 10/1997 | Root | 600/35 |

*Primary Examiner*—John P. Lacyk
*Assistant Examiner*—Samuel Gilbert
*Attorney, Agent, or Firm*—Henderson & Sturm

[57] ABSTRACT

An artificial insemination device and process for animals and mammals having an elongated, hollow catheter tube adapted for attachment in a bonded manner at one end with an annular, bulbous tip, the tip having a axial passage formed therethrough and with a balloon having perforations formed therein at one closed end and having an opposite, open end affixed in a bonded manner with the tip, whereby fluid may flow from the tube through the tip and into the balloon for ejection through the perforations caused by uterine contractions of an animal being artificially inseminated, the combination acting upon the inflated balloon. The balloon is capable of being tucked within the tip passage prior to and during insertion into the animal. A semen container is attachable to an opposite end of the catheter tube, with a device associated with the tube opposite end for allowing the flow of semen only from the container toward the balloon.

9 Claims, 3 Drawing Sheets

DEVICE AND PROCESS FOR ARTIFICIAL INSEMINATION OF ANIMALS

CROSS-REFERENCE TO RELATED APPLICATIONS

Not applicable.

STATEMENT REGARDING FEDERALLY SPONSORED RESEARCH OR DEVELOPMENT

Not applicable.

MICROFICHE APPENDIX

Not applicable.

BACKGROUND OF THE INVENTION

1. Field of the Invention

The present invention pertains to a device adapted to be used in the practice of artificial insemination of animals and mammals.

2. Description of the Prior Art

Artificial insemination of animals and humans rather than natural propagation is well known in the art and has many advantages which accrue from the use of this method. U.S. Pat. No. 3,256,884 entitled "Injection Device for Artificial Insemination Having a Disposable Dispensing Capsule with Detachable Actuator" issued on Jun. 21, 1966 to Harold J. Hill sets out the conventional procedure of that time period. A more contemporary treatise is provided by the publication *The Swine Al Book*, Copyright 1994, U.S. Copyright Office No. ISBN0-964 0737-0-6, publisher Morgan Morrow BVScMSPhD, Department of Animal Science, North Carolina State University, Raleigh, N.C. 27695-7621, USA.

SUMMARY OF THE INVENTION

The contemporary artificial insemination applicator device comprises two units which are normally connected to each other during the procedure; a container for holding a predetermined quantity of semen, and a catheter comprising an elongated, semi-rigid tube with an ejection tip formed on one end thereof. The elongated tube normally has a smooth outer surface, and by using sufficient tensile stress applied thereto by hand, can be bent in an arc.

The ejection tip has several common shapes: one, an enlarged bulbous shape is formed with at least a pair of ridges on its exterior surface; others are similarly formed with external spiraled shapes. All tips are hollow to receive and to be bonded in one manner or another to one end of the catheter.

The container may be: a flexible bottle having a cap with a tip insertable into the other end of the tube; a flexible toothpaste-type tube with a similar tip; or a crochet bag adapted to receive the other free end of the tube for transmitting semen from the bag, through the tube and into the ejection tip. Both the tube and tip are normally of a nontoxic, resinous material.

A conventional procedure for artificial insemination places the host animal, such as a sow, for example, within a small confinement such that the operator may stand near to the sow. As the sow is in heat, regardless of efforts to quiet her—such as placing her next to a boar in an adjacent stall, she may have a tendency to move about during the process. Further, much tail swinging occurs with disastrous results as seen hereafter. Should it be necessary, as where labor intensity is involved, for the operator to be inseminating a pair of sows in the same enclosure at the same time, such problems are exacerbated. After lubricating the ejection tip with a non-spermicidal jelly, the vulva lips of the sow are opened such that the ejection tip can be inserted forward and upward into the vagina as shown in FIG. 5. This penetration and thrust of the ejection tip mimics the movement of a boar's penis, the upward nature of the thrust required to a degree by the upward slant of the vagina.

With the cervix of the animal upstream of the vagina, and as a part of the uterine cavity having rings (villosities) formed therein, and with the object of locking the ejection tip into the cervix, contemporary ejection tips with a series of external spirals formed thereon requires that the catheter is rotated (counter-clockwise as it were) to properly insert the ejection tip into the cervix. Or, another form of ejection tip is of a bulbous nature, having one or more rings, which type of tip is more pushed or forced into the cervix, rather than twisted. Once within the cervix, the operator may feel the constriction of the cervix rings about the tip, the "feel" enhanced by a slight back pressure upon the tube which he/she is holding. One test is to pull back slightly on the tube; if, of course, it pulls out, reinsertion must be made, if not, the insertion is complete.

At this time, as the contemporary tube of approximate 20" in length and made of a nontoxic plastic material is semi-rigid but deformable, and incapable of retaining a bent position, the outer free end of the tube extends rearwardly and slightly downwardly from the rear end of the sow. The operator must then grab the tube free end with one hand, bend its shank or middle portion upward, and manipulate the semen container with the other to join the free end to the container and then to hold the container above and normally behind the sow. In this condition, a gravity flow of semen from the container, through the tube and tip and into the cervix will occur, with uterine contractions caused by the insertion of the tip providing suction within the cervix which primarily causes the transmission of semen into the cervix. Although the container may be manually squeezed, too much pressure may force semen back out of the vulva, thus wasting it.

Once this all has been accomplished, the insemination may then be completed within, for example, another 5–10 minutes, the operator still holding the container above and behind the sow at all times.

Contemporary artificial insemination units which utilize only the insertion of the tip into the animals' cervix present several problems. Due to inability of the recipient animal to absorb or take up large amounts of semen in a short amount of time, expulsion or flow-back of the semen past and to the rear of the tip occurs; thus wasting semen, reducing the effectiveness of the semen due to quantity loss, and increasing the length of time of the process, thus causing more fatigue of the technician. Expulsion can also be caused by the recipient not being able to clamp down on the tip and create a seal on the typical "one-size-fits-all" catheter tips.

As mentioned hereinbefore, artificial insemination technicians can become bored and/or fatigued and actually force the semen into the recipient, which pressurizes the cervix and can break the seal of the cervix on the catheter tip and cause expulsion.

Another problem with conventional artificial insemination is the length of time required to complete each insemination. Swine, for example, can take anywhere from 3–5 minutes or longer per animal to inseminate. Although there are devices to assist the technician in inseminating, such as a back-strap to hold semen reservoir and catheter tip, these devices must be monitored very closely by technicians to prevent adjoining animals from tearing them off or dislodging the catheter from the recipient.

Due to the conventional need for maintaining the container connected to the catheter, several disadvantages occur. For example, upon bending the tube upwardly about the shank or mid-zone of the tube for having the container held above the animal, the inflexibility of the tube tends to force the tube portion and tip within the animal into a non-normal position, tending to oblong the muscular discs of the cervix which in turn breaks the seal around the tip and allows leakage or flow-back of the semen out of the animal. Also, the tip discharge opening may be obstructed within the cervix.

Additionally, the catheter tube and container are usually placed in a position adjacent the tail of the sow. Experience has shown that swishing of the tail has sufficient force to either dislodge the catheter from the cervix, or to separate the catheter tube from the container. Further, the inflexibility of the contemporary tube makes unassisted insemination, a strapping or non-manual attaching of the container on the back of the animal extremely difficult, due particularly to the tendency to dislodge or change the normal position of the tip.

Lastly, but importantly, the relative inflexibility of the contemporary catheter tube requires the operator to assume and maintain an awkward posture in order to hold the container in its raised position during insemination, partly due to the difficulty of bending and then trying to hold the tube in an upright position.

The aforementioned procedure, although specifically described for animals, is applicable in the appropriate environment for use with mammals.

It is to overcome these disadvantages of the contemporary art that this invention is directed.

An object of this invention is to provide an improved artificial insemination device for animals, and a method of use thereof.

Yet another object of this invention is to provide an artificial insemination device including an inflatable balloon with a perforated forward end attached to the forward end of the catheter tip for insertion into the animal.

It is another object of this invention to provide an artificial insemination device for animals which tends to ensure a gradual, more natural discharge of semen within the cervix during the process, and without the need of the technician holding the reservoir.

Still another object of this invention is to reduce leakage or "flow back" of semen from the catheter tip within the animal during the process.

Yet another object of this invention is to provide for a more efficient use and flow of the semen from the catheter tip into the cervix of the animal.

It is another object of this invention to provide an artificial insemination device which effects an improved sealing of the cervix to substantially reduce flow-back of the semen past the catheter tip, thus enhancing the effectiveness of the.

It is another object of this invention to provide an improved method of artificial insemination of an animal wherein during the process the semen container may be removed from the outer end of the catheter tube immediately after a predetermined amount of semen has been evacuated therefrom, thus obviating all of the disadvantage of the container attached to a relatively inflexible catheter tube.

Yet another object of this invention is to provide an artificial insemination device which eliminates the need for continued manipulation of the container during the insemination process.

Still another object of this invention is to lessen the normal fatigue of the technician utilizing the artificial insemination equipment, thus enhancing the effectiveness of use thereof.

BRIEF DESCRIPTION OF THE SEVERAL VIEWS OF THE DRAWINGS

These and other attributes of the invention will become more clear upon making a thorough review and study of the following description of a preferred embodiment, particularly when reviewed in conjunction with the drawings, wherein.

DETAILED DESCRIPTION OF THE INVENTION

Figure 1:
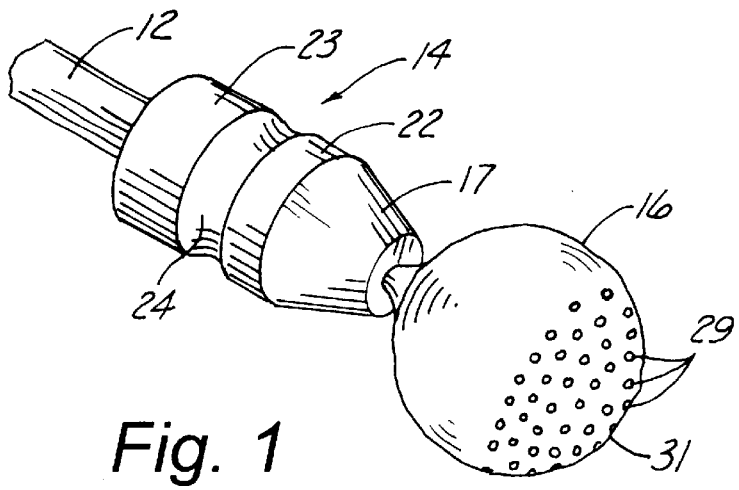
FIG. 1 is a perspective view showing the outer end of a catheter tube and a tip attached thereto of contemporary construction, but with a semen ejecting balloon applied thereto of the present invention.
Figure 2:
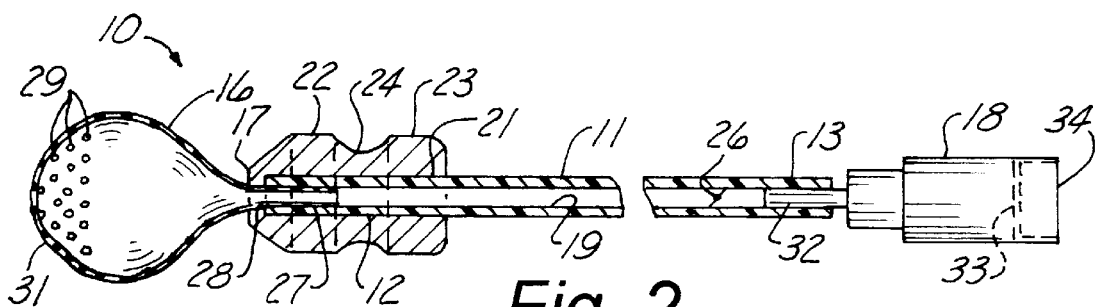
FIG. 2 is a reduced foreshortened view, partly in section, showing one embodiment of the entire artificial insemination device of FIG. 1.

Referring particularly to FIGS. 1 and 2, the artificial insemination device of this invention is indicated generally at (10) and comprises: a catheter tube (11) having opposed ends (12), (13); a tip (14) at one end (12) with an ejector balloon (16) affixed within the forward end (17) of the tip (14), and a semen container (18) detachably inserted into the opposite end (13) of the catheter tube (11).

More specifically, the catheter tube (11) is of an approximate twenty inches in length, with a constant, predetermined O.D. and a constant I.D., thus forming a fluid passage (19) therethrough, providing for the semen, or other fluid, to readily flow through the passage (19). The tube (11) is hollow, of a relatively rigid, non-toxic, non-spermicidal plastic material, and may be flexed or curved when required.

At the forward tube end (12), the tip (14) is adhesively bonded or ultrasonically welded thereto so as to fully embrace the end (12), an internal passage (21) being formed through the tip (14) for receiving the catheter end (12). Similar to the tube (11), the tip (14) may be composed of any flexible, deformable non-toxic plastic or like material, and has a bulbous external shape formed by a pari of longitudinally spaced, annular ridges (22), (23) with an annular groove (24) formed therebetween. The leading face (26) of the tip (14) is of a conical shape for ease of entry into the animal to be inseminated.

The ejector balloon (16) is also of a non-toxic, non-spermicidal, elastomeric product capable of many inflations and deflations, although in use it is contemplated to have only a single use and then discarded. The open end (27) of the balloon (16) is secured in any suitable manner within the passage (19) of the catheter tube end (17) as illustrated in FIG. 2. The manner of securement of the end (27) could be by adhesive, crimping, ultrasonic welding or the like, and allows the semen fluid (not shown) to pass outwardly from the tip (11) into the interior of the balloon (16). When initially assembled, the entire balloon (16) is folded or tucked completely within the forward end (17) of the catheter tube (11). Should the end (17) not extend completely through the tip passage (21), such that a forward portion (28) of the passage (21) remains, it is possible that the balloon (16) may instead be folded or tucked within the portion (28), and it is also possible that the open end (27) of the balloon may be secured within the portion (28) for fluid passage through the catheter tube forward end (17), then through the tip passage forward portion (28), and then into the balloon (16) when desired.

For ejection of semen from the balloon (16) in use, perforations (29) are formed within the periphery of the forward portion of the closed end (31) of the balloon opposite the open end (27). The number and size of perforations (20) are such that upon sufficient semen, such as 10 ml., being forced into the balloon (16) to cause its inflation as shown in FIGS. 1 and 2, a gradual flow of semen through the perforations (29) to exterior the balloon (16) will occur.

To provide for a predetermined amount of semen to be received by the balloon (16) for expulsion therefrom the container (18) is provided. The container (18) is of a conventional structure, usually a non-toxic, non-spermicidal plastic deformable material having a needle-type tip (32) for removable insertion into the passage (19) of the catheter tube end (13). In another embodiment, rather than the manual squeeze-type container (19), it may be more rigid similar to a cartridge, with a piston (33) inserted within the rear end (34); for use, for example, with a conventional dispersing gun (not shown). Should it be desirable to remove the container (19) from the catheter tube (11) during the insemination process, a one-way valve (36), for example, may be inserted into the catheter tube end (13), such that the semen or other fluid may flow from the container (18) forwardly through the tube passage (19), but may not flow in a reverse direction past he valve (26).

Figure 3:
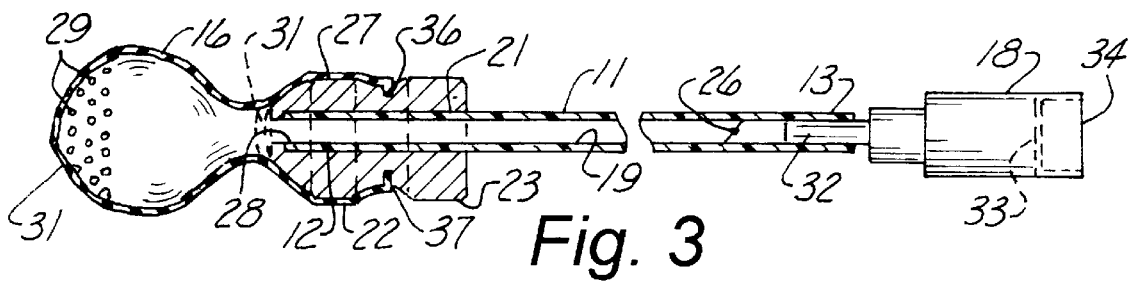
FIG. 3 is a view similar to FIG. 1 and showing a second embodiment of the device of FIG. 2.

A second embodiment of the invention is shown in FIG. 3 wherein the open end (27) of the balloon (16) embraces and is adhered about a forward portion of the tip (14), covering, for example, the leading face (26) of the tip (14), one of the ridges (22), and the groove (24). The method of adherence could be any conventional manner of bonding, and if necessary, an annular cut (36) could be made in the groove (24), for example, to receive the annular edge (37) of the balloon end (27). When deflated and prior to use, the forward end (31) of the balloon (16) may embrace the forward end (17) of the tip (14), as shown by dotted lines in FIG. 3. This arrangement is applicable to the other embodiments, as well.

Figure 4:
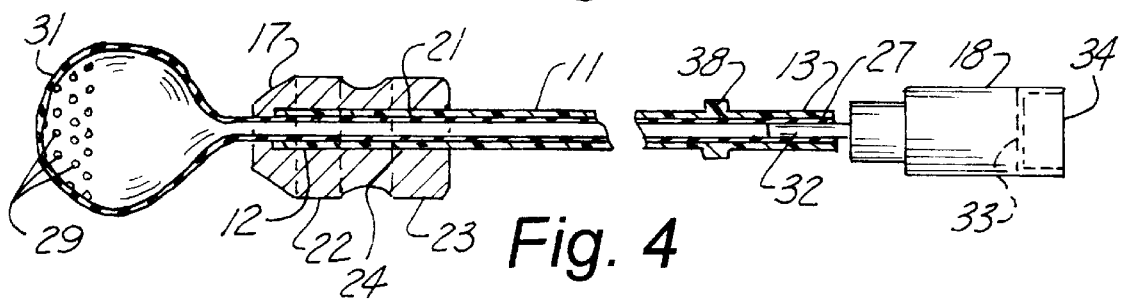
FIG. 4 is a view similar to FIG. 3, an showing a third embodiment of the device.

A third embodiment is shown in FIG. 4 wherein the balloon has a lengthened end (38) which extends substantially through the tube passage (19) and is adhered thereto by any conventional means and manner such that semen may flow therethrough from the container tip (32). Although a one-way valve (26) is shown for the embodiments of FIGS. 2 and 3, other devices for permitting such one-way passage of the semen are contemplated for the embodiment of FIG. 2, such as a duck-bill vent (not shown) or a clamp (38).

Figure 6:
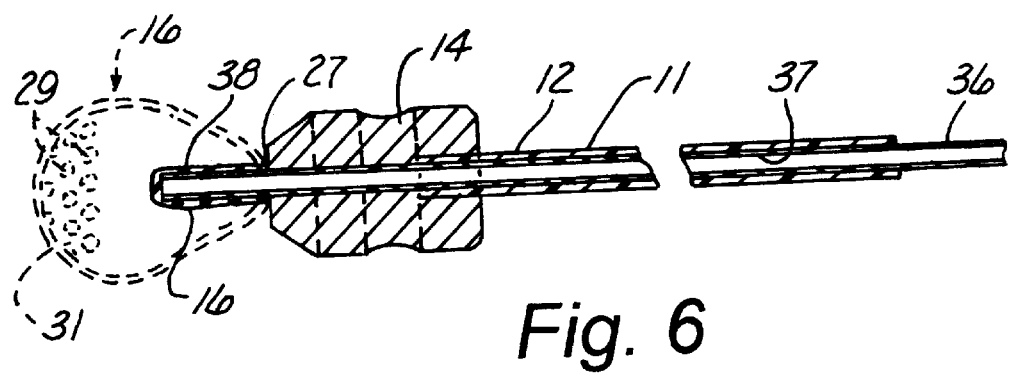
FIG. 6 is a view similar to FIG. 2, and showing a fourth embodiment of the device.

FIG. 6 discloses another embodiment of the invention, wherein a disposable, catheter tube (36) of a smaller diameter, with a fluid passage (37) formed therethrough, and of material similar to the catheter tube (11) is inserted within and through the main tube (11), and with a forward portion (38) of the secondary tube (36) extended beyond the tip (14) and secured to the portion (28). With the balloon (16) affixed initially within the forward position or end (38) for insertion within the vagina as before, upon manipulation of the container (18), the balloon (16) is inflated by the semen forced therein, and the semen is subsequently expelled through the perforations (29) due to the uterine contractions acting upon the balloon (16). Should it be desirable to ascertain if the balloon (16) has become deflated whereby the semen is fully expelled, the technician may tug upon the disposable tube (36). If still inflated, resistance to a withdrawal of the tube (36) indicates semen remains within the balloon (16).

Further, it is readily apparent that the main tube (11) may be withdrawn from the uterus, leaving the disposable tube (36) and the balloon (16) for continued manipulation.

Figure 5:
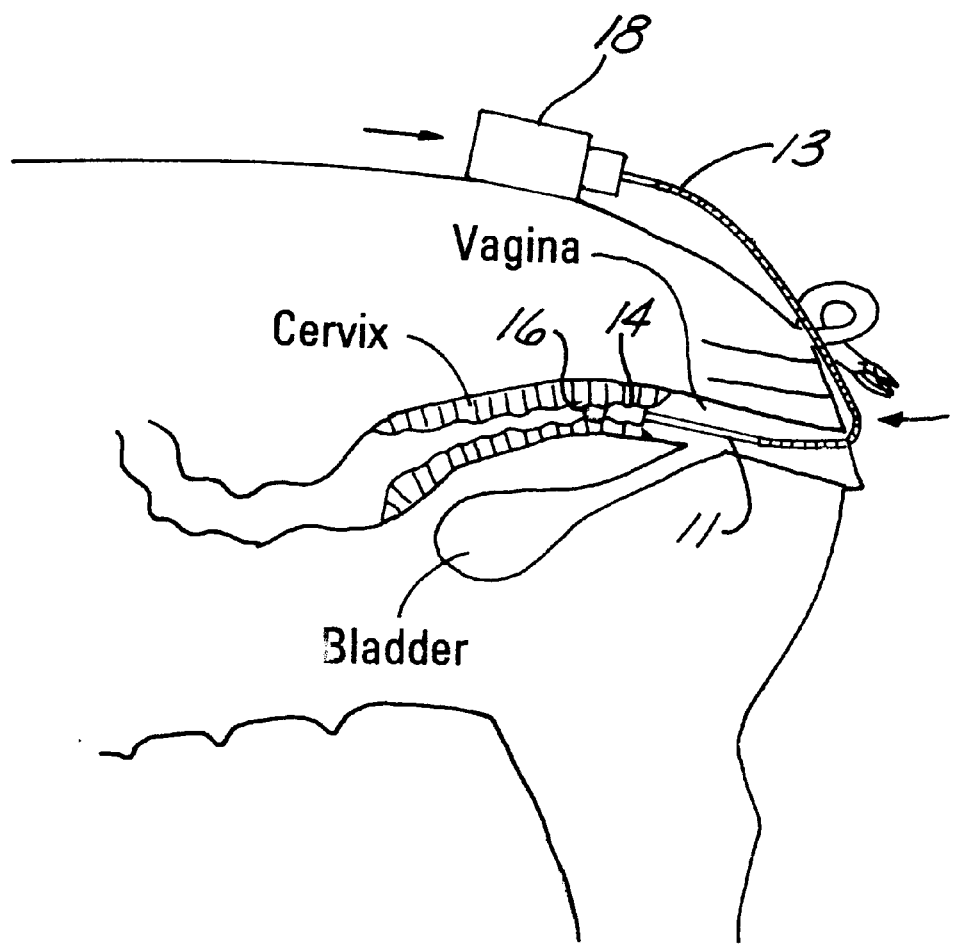
FIG. 5 is a schematic of an animal, showing the placement of the catheter, tip, and the balloon ejector into the cervix of the animal.

In use, the catheter tip (14) with the balloon (16) tucked therein (see FIG. 5 but wherein the balloon (16) is expanded)) is inserted within the vagina of the animal by placing the tip (14), to which had previously been applied a non-spermicidal sterile lubricating jelly, within the vulva lips and firmly pushing the tip (14) forwardly and upwardly through the vagina until the operator can tell that the tip (14) has entered the cervix of the animal, such that the cervical rings have clamped down upon the tip (26).

The next step of the insemination process involves a bending of the tube (11) upwardly by the operator for ease of attaching it to the semen container (18). For assisted mating by the operator, the container (18) is normally held with the tube (11) substantially upright or vertical for enhancing flow by gravity of the semen through the tube (11) to the ejection tip (14). At the tip (14) and without the balloon, ejection occurs mostly due to the recurring uterine contractions, thus aiding the withdrawal of semen through the tip (14) and into the cervix (FIG. 5). Further, without the provision of the balloon (16), to attempt to eliminate the problems noted hereinbefore caused by the swishing of the tail, or movement of the animal about its enclosure, contemporary procedures include strapping or otherwise attaching the container (18) to the back of the animal as shown in FIG. 5.

Importantly, by the provision of the balloon (16) initially tucked within the tip (14), with the tip (14) inserted into the cervix of the animal, and the container (18) connected to the catheter tube end (13), and filled with a predetermined amount of semen, manipulation of the container (18) will effect a flow of a pre-desired amount, 10 ml. To 100 ml. For example, of semen through the tube (11) and tip (14) and into the balloon (16), thus causing the balloon (16) to expand to a condition outside the tip (14), forwardly thereof, and into the cervix as best shown in FIG. 5. The container (18) may then be withdrawn from the catheter tube (11), with the tube (11) at the far end (13) either clamped off, or merely left free, flow back prevented due to the one-way valve (26) or other flow restriction means. Another advantage is that there is no reservoir or semen container (18) to be dislodged from the catheter (11) by swishing tails. The expansion of the balloon (16) and the holes or perforations (29) in the balloon (16) restrict the flow of semen and allow for a much more natural, gradual insemination. The contractions of the recipient's uterus, coupled with the resilience of the balloon (16), thus allows for withdrawal of semen from the balloon (16).

The gradual release of semen from the balloon (16) will drastically reduce expulsion or flow-back. The form fitting ability of the balloon (16) will contour to fit most any size recipient and keep the cervical opening sealed during insemination to reduce or eliminate expulsion. The balloon (16) can be expanded and then left alone for 3–10 minutes for the recipient to "milk" the balloon (16), thus inseminating herself. This allows the technician to be doing other things instead of tiring and trying to rush the procedure. The fact that there is no external reservoir or back-strap makes it improbable that adjoining animals could bother or dislodge, catheter tubes from those being inseminated.

As various sperm products may have various viscosities, the size of the balloon perforations (29) may depend upon the viscosity and the length of time the operator or technician prefers to have for the insemination process. When ascertained that the balloon (16) is empty, the catheter tube (11), tip (14) and balloon (16) may be withdrawn from the animal. Or, if necessary to insert more semen into the animal, the container (18), if having been removed from the tube end (13), may be reinserted, and another quantity of semen may be inserted into the balloon (16) for re-inflation and expulsion through the perforations (29) by the animal's uterine contractions, acting upon the inflated balloon (16).

What is claimed is:

1. An artificial insemination device comprising:
   an elongated, hollow tube having opposed ends;
   a container for holding an amount of semen therein, said container removably attached to one end of said tube;
   a hollow, bulbous tip having a passage formed therein attached to the opposite end of said tube, whereby semen may flow from said container into said tube and through said tip passage; and
   expandable means attached to said tip for receiving semen therefrom, said means expandable outwardly and forwardly from said tip in an expanded condition upon receipt of the semen, and for ejecting the semen forwardly of said tip while in said expanded condition.

2. The artificial insemination device of claim 1, and further wherein said expandable means is foldable into said tip passage prior to use thereof.

3. The artificial insemination device of claim 2, and further wherein said expandable means comprises an inflatable balloon.

4. The artificial insemination device of claim 3, and further wherein said balloon has an open end secured within said tip passage for receiving semen therefrom.

5. The artificial insemination device of claim 4, and further wherein said balloon has a closed end with perforations formed therein, whereby semen may flow outwardly of said balloon through said perforations.

6. The artificial insemination device of claim 3, and further wherein said balloon has an open end which embraces said tip for receiving semen therefrom.

7. The artificial insemination device of claim 6, further wherein said balloon has a closed end with perforations formed therein, whereby semen may flow outwardly of said balloon through said perforations.

8. The artificial insemination device of claim 3, and further wherein said balloon has an open end secured within said hollow tube for receiving semen therefrom.

9. The artificial insemination device of claim 8, and further wherein said balloon has a closed end with perforations formed therein, whereby semen may flow outwardly of said balloon through said perforations.

* * * * *